US012643111B2

(12) United States Patent　　　(10) Patent No.:　US 12,643,111 B2
Batchelor et al.　　　　　　　　　(45) Date of Patent:　　Jun. 2, 2026

(54) NANO SURFACES ON SMOKE PARTICLE ELECTRODES

(71) Applicant: GYRUS ACMI, INC., Westborough, MA (US)

(72) Inventors: Kester Julian Batchelor, Mound, MN (US); John Mensch, Plymouth, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 668 days.

(21) Appl. No.: 18/047,184

(22) Filed: Oct. 17, 2022

(65) Prior Publication Data

US 2023/0133254 A1　　May 4, 2023

Related U.S. Application Data

(60) Provisional application No. 63/262,929, filed on Oct. 22, 2021.

(51) Int. Cl.
| | |
|---|---|
| *A61B 18/14* | (2006.01) |
| *A61B 18/00* | (2006.01) |
| *A61B 18/12* | (2006.01) |
| *B03C 3/38* | (2006.01) |
| *B03C 3/41* | (2006.01) |
| *B03C 3/64* | (2006.01) |

(52) U.S. Cl.
CPC ................ *B03C 3/38* (2013.01); *A61B 18/14* (2013.01); *B03C 3/41* (2013.01); *B03C 3/64* (2013.01); *A61B 2018/00125* (2013.01); *A61B 2018/0013* (2013.01); *A61B 2018/1266* (2013.01); *B03C 2201/26* (2013.01)

(58) Field of Classification Search
CPC .......... A61B 18/14; A61B 2018/00125; A61B 2018/0013; A61B 2018/1266; B03C 3/38; B03C 3/41; B03C 2201/26
See application file for complete search history.

(56) References Cited

U.S. PATENT DOCUMENTS

| | | |
|---|---|---|
| 4,542,461 A | 9/1985 | Eldridge et al. |
| 5,669,904 A | 9/1997 | Platt, Jr. et al. |
| 6,213,999 B1 | 4/2001 | Platt, Jr. et al. |

(Continued)

FOREIGN PATENT DOCUMENTS

| | | |
|---|---|---|
| CN | 1193268 | 9/1998 |
| CN | 1750794 | 3/2006 |

(Continued)

OTHER PUBLICATIONS

"U.S. Appl. No. 14/865,420, Decision on Pre-Appeal Brief Request mailed Jul. 11, 2019", 2 pgs.

(Continued)

*Primary Examiner* — Joseph A Stoklosa
*Assistant Examiner* — Annie L Stoklosa
(74) *Attorney, Agent, or Firm* — Schwegman Lundberg & Woessner, P.A.

(57) ABSTRACT

Various embodiments disclosed relate to a device and methods for electrosurgery, where the device end effector includes an anti-smoke layer. The present disclosure includes a device having first and second electrodes that include the anti-smoke layer, which can be a hydrophobic layer to aid in reduction of smoke production during operation.

15 Claims, 5 Drawing Sheets

(56)  References Cited

U.S. PATENT DOCUMENTS

| | | | |
|---|---|---|---|
| 6,623,544 B1 | 9/2003 | Kaura | |
| 8,357,155 B2 * | 1/2013 | Heim | A61B 18/1402 |
| | | | 606/41 |
| 9,308,366 B2 | 4/2016 | Warren et al. | |
| 9,925,372 B2 | 3/2018 | Amoah et al. | |
| 10,722,294 B2 | 7/2020 | Griffiths et al. | |
| 11,020,166 B2 | 6/2021 | Batchelor et al. | |
| 11,076,909 B2 | 8/2021 | Batchelor et al. | |
| 12,144,535 B2 | 11/2024 | Batchelor et al. | |
| 12,156,690 B2 | 12/2024 | Batchelor et al. | |
| 2003/0130658 A1 | 7/2003 | Goble et al. | |
| 2004/0030330 A1 | 2/2004 | Brassell et al. | |
| 2004/0116918 A1 | 6/2004 | Konesky | |
| 2005/0154385 A1 | 7/2005 | Heim et al. | |
| 2005/0171528 A1 | 8/2005 | Sartor et al. | |
| 2006/0025757 A1 | 2/2006 | Heim | |
| 2006/0217706 A1 | 9/2006 | Lau et al. | |
| 2007/0299439 A1 | 12/2007 | Latterell et al. | |
| 2008/0108985 A1 | 5/2008 | Konesky | |
| 2010/0100091 A1 | 4/2010 | Truckai | |
| 2011/0046619 A1 * | 2/2011 | Ducharme | A61B 18/1477 |
| | | | 606/41 |
| 2011/0295250 A1 | 12/2011 | Johnson et al. | |
| 2011/0306006 A1 | 12/2011 | Holbeche et al. | |
| 2012/0065635 A1 | 3/2012 | Konesky | |
| 2012/0067212 A1 * | 3/2012 | Warren | A61B 18/00 |
| | | | 95/57 |
| 2012/0116384 A1 | 5/2012 | Truckai | |
| 2013/0074790 A1 | 3/2013 | Rabhi | |
| 2013/0116682 A1 * | 5/2013 | Koo | C23C 16/513 |
| | | | 606/41 |
| 2014/0005663 A1 | 1/2014 | Heard et al. | |
| 2014/0228836 A1 | 8/2014 | Amoah et al. | |
| 2014/0246471 A1 | 9/2014 | Jaworek et al. | |
| 2014/0249557 A1 | 9/2014 | Koch, Jr. et al. | |
| 2014/0276407 A1 * | 9/2014 | DeVries | A61B 18/16 |
| | | | 604/103.08 |
| 2014/0276795 A1 | 9/2014 | Batchelor et al. | |
| 2014/0303615 A1 | 10/2014 | Amoah | |
| 2014/0364844 A1 | 12/2014 | Van Wyk | |
| 2015/0182708 A1 | 7/2015 | Barnard | |
| 2015/0201999 A1 | 7/2015 | Hassler, Jr. | |
| 2017/0086915 A1 | 3/2017 | Batchelor et al. | |
| 2017/0151012 A1 | 6/2017 | Griffiths et al. | |
| 2018/0014316 A1 | 1/2018 | Guo et al. | |
| 2018/0206905 A1 * | 7/2018 | Batchelor | A61B 18/14 |
| 2019/0178510 A1 | 6/2019 | Lin et al. | |
| 2019/0247141 A1 | 8/2019 | Batchelor et al. | |
| 2021/0007789 A1 | 1/2021 | Boucher et al. | |
| 2021/0251682 A1 | 8/2021 | Batchelor et al. | |
| 2021/0259764 A1 | 8/2021 | Batchelor et al. | |

FOREIGN PATENT DOCUMENTS

| | | | |
|---|---|---|---|
| CN | 101022768 | | 8/2007 |
| CN | 101056593 | | 10/2007 |
| CN | 102164556 | | 8/2011 |
| CN | 102202591 | | 9/2011 |
| CN | 102470009 | A | 5/2012 |
| CN | 103222893 | | 7/2013 |
| CN | 103796604 | | 5/2014 |
| CN | 103930212 | A | 7/2014 |
| CN | 204133601 | | 2/2015 |
| CN | 204158485 | | 2/2015 |
| CN | 104519820 | | 4/2015 |
| CN | 108024829 | A | 5/2018 |
| CN | 108024829 | B | 3/2021 |
| CN | 112998840 | A | 6/2021 |
| CN | 214259454 | | 9/2021 |
| CN | 112998840 | | 5/2024 |
| EP | 1449487 | | 8/2004 |
| EP | 2531132 | A1 | 12/2012 |
| EP | 3324868 | A1 | 5/2018 |
| EP | 3324868 | B1 | 6/2020 |
| EP | 3744276 | B1 | 3/2022 |
| GB | 2613452 | | 6/2024 |
| JP | H05184589 | A | 7/1993 |
| JP | H09503423 | A | 4/1997 |
| JP | 2001137319 | A | 5/2001 |
| JP | 2012533380 | A | 12/2012 |
| JP | 2014534870 | A | 12/2014 |
| JP | 2018528011 | A | 9/2018 |
| JP | 6585834 | B2 | 10/2019 |
| WO | WO-9609118 | A1 | 3/1996 |
| WO | WO-9627337 | A1 | 9/1996 |
| WO | WO-9915091 | A1 | 4/1999 |
| WO | 9940858 | | 8/1999 |
| WO | WO-2008135736 | A1 | 11/2008 |
| WO | WO-2011010148 | A2 | 1/2011 |
| WO | 2011092464 | | 8/2011 |
| WO | WO-2013045866 | A2 | 4/2013 |
| WO | WO-2013045886 | A1 | 4/2013 |
| WO | WO-2014152059 | A1 | 9/2014 |
| WO | WO-2016024130 | A1 | 2/2016 |
| WO | WO-2017053945 | A1 | 3/2017 |

OTHER PUBLICATIONS

"U.S. Appl. No. 14/865,420, Final Office Action mailed Mar. 8, 2019", 9 pgs.

"U.S. Appl. No. 14/865,420, Final Office Action mailed Oct. 30, 2020", 9 pgs.

"U.S. Appl. No. 14/865,420, Final Office Action mailed Dec. 10, 2019", 10 pgs.

"U.S. Appl. No. 14/865,420, Non Final Office Action mailed Jun. 1, 2018", 9 pgs.

"U.S. Appl. No. 14/865,420, Non Final Office Action mailed Jun. 12, 2020", 10 pgs.

"U.S. Appl. No. 14/865,420, Notice of Allowance mailed Feb. 5, 2021", 7 pgs.

"U.S. Appl. No. 14/865,420, Pre-Appeal Brief Request filed Jun. 10, 2019", 6 pgs.

"U.S. Appl. No. 14/865,420, Response filed Jan. 21, 2020 to Final Office Action mailed Oct. 30, 2020", 8 pgs.

"U.S. Appl. No. 14/865,420, Response filed Mar. 10, 2020 to Final Office Action mailed Dec. 10, 2019", 10 pgs.

"U.S. Appl. No. 14/865,420, Response filed Jun. 10, 2019 to Final Office Action mailed Mar. 8, 2019", 9 pgs.

"U.S. Appl. No. 14/865,420, Response filed Jul. 16, 2020 to Non Final Office Action mailed Jun. 12, 2020", 8 pgs.

"U.S. Appl. No. 14/865,420, Response filed Nov. 26, 2018 to Non Final Office Action mailed Jun. 1, 2018", 9 pgs.

"U.S. Appl. No. 14/865,420, Supplemental Notice of Allowability mailed Mar. 3, 2021", 3 pgs.

"U.S. Appl. No. 14/865,420, Supplemental Notice of Allowability mailed May 5, 2021", 3 pgs.

"U.S. Appl. No. 15/747,905, Corrected Notice of Allowability mailed May 20, 2021", 3 pgs.

"U.S. Appl. No. 15/747,905, Corrected Notice of Allowability mailed Jun. 28, 2021", 3 pgs.

"U.S. Appl. No. 15/747,905, Non Final Office Action mailed Jan. 7, 2021", 13 pgs.

"U.S. Appl. No. 15/747,905, Notice of Allowance mailed Feb. 10, 2021", 8 pgs.

"U.S. Appl. No. 15/747,905, Preliminary Amendment filed Jan. 26, 2018", 10 pgs.

"U.S. Appl. No. 15/747,905, Response filed Jan. 21, 2021 to Non Final Office Action mailed Jan. 7, 2021", 13 pgs.

"U.S. Appl. No. 15/747,905, Supplemental Notice of Allowability mailed Mar. 4, 2021", 3 pgs.

"U.S. Appl. No. 17/306,402, Notice of Non-Compliant Amendment mailed May 28, 2021", 2 pgs.

"U.S. Appl. No. 17/306,402, Preliminary Amendment filed May 24, 2021", 6 pgs.

"U.S. Appl. No. 17/306,402, Response filed Jul. 28, 2021 to Notice of Non-Compliant Amendment mailed May 28, 2021", 3 pages.

"U.S. Appl. No. 17/314,211, Notice of Non-Compliant Amendment mailed May 28, 2021", 2 pgs.

(56)  References Cited

OTHER PUBLICATIONS

"U.S. Appl. No. 17/314,211, Preliminary Amendment filed May 21, 2021", 6 pgs.

"U.S. Appl. No. 17/314,211, Response filed Jul. 28, 2021 to Notice of Non-Compliant Amendment mailed May 28, 2021", 3 pages.

"Chinese Application Serial No. 201680054565.5, Office Action mailed Apr. 3, 2020", w/ English translation, 18 pgs.

"Chinese Application Serial No. 201680054565.5, Office Action mailed Aug. 17, 2020", w/ English Translation, 15 pgs.

"Chinese Application Serial No. 201680054565.5, Response Filed Jun. 10, 2020 to Office Action mailed Apr. 3, 2020", w/ English Claims, 66 pgs.

"Chinese Application Serial No. 201680054565.5, Response filed Oct. 15, 2020 to Office Action mailed Aug. 17, 2020", w/ English Claims, 17 pgs.

"European Application Serial No. 16778611., Communication to the Parties Concerning Termination of Opposition Proceedings mailed Sep. 13, 2022", 1 pg.

"European Application Serial No. 16778611.0, Communication Pursuant to Article 94(3) EPC mailed Dec. 3, 2018", 7 pgs.

"European Application Serial No. 16778611.0, Decision Rejecting the Opposition (Art. 101(2) EPC) mailed May 27, 2022", 21 pgs.

"European Application Serial No. 16778611.0, Intention to Grant mailed Jan. 16, 2020", 138 pgs.

"European Application Serial No. 16778611.0, Notice of Opposition mailed Mar. 31, 2021", 23 pgs.

"European Application Serial No. 16778611.0, Response filed Apr. 30, 2019 to Communication Pursuant to Article 94(3) EPC mailed Dec. 3, 2018", 60 pgs.

"European Application Serial No. 16778611.0, Response filed Jun. 29, 2021 to Notice of Opposition mailed Mar. 31, 2021", 147 pgs.

"European Application Serial No. 16778611.0, Response to Opponent's Submission filed Apr. 12, 2022", 5 pgs.

"European Application Serial No. 16778611.0, Summons to Attend Oral Proceedings mailed Oct. 13, 2021", 11 pgs.

"European Application Serial No. 20178054.1 Response filed Aug. 12, 2021", 6 pgs.

"European Application Serial No. 20178054.1, Communication Pursuant to Rule 114(2) EPC mailed Jun. 9, 2021", 10 pgs.

"European Application Serial No. 20178054.1, Extended European Search Report mailed Oct. 29, 2020", 6 pgs.

"European Application Serial No. 20178054.1, Response filed May 24, 2021 to Extended European Search Report mailed Oct. 26, 2020", 3 pgs.

"Force FX™-C Electrosurgical Generator with Instant Response™ Technology", Valleylab, [Online]. Retrieved from the Internet: <URL: https://www.equippedmd.com/wp-content/uploads/2018/01/Valleylab-Force-FX-C-Operators-Guide.pdf>, (2009), 118 pgs.

"International Application Serial No. PCT/US2016/053717, International Preliminary Report on Patentability mailed Apr. 5, 2018", 9 pgs.

"International Application Serial No. PCT/US2016/053717, International Search Report mailed Dec. 9, 2016", 5 pgs.

"International Application Serial No. PCT/US2016/053717, Written Opinion mailed Dec. 9, 2016", 7 pgs.

"Japanese Application Serial No. 2018-514989, Amendment filed Mar. 20, 2018", W/ English Translation, 7 pgs.

"Japanese Application Serial No. 2018-514989, Amendment filed Apr. 3, 2018", W/ English Translation, 27 pgs.

"Japanese Application Serial No. 2018-514989, Decison to Grant Aug. 6, 2019", W/English Translation, 5 pgs.

"Japanese Application Serial No. 2018-514989, Notice of Reason for Rejection mailed Jan. 29, 2019", W/English Translation, 8 pgs.

"Japanese Application Serial No. 2018-514989, Response filed May 30, 2019 to Notice of Reason for Rejection mailed Jan. 29, 2019", W/ English Translation, 42 pgs.

"Japanese Application Serial No. 2019-161878, Amendment filed Oct. 3, 2019", W/English Translation, 26 pgs.

"Japanese Application Serial No. 2019-161878, Notification of Reasons for Rejection mailed Dec. 22, 2020", w/ English Translation, 12 pgs.

"Japanese Application Serial No. 2019-161878, Response filed Mar. 10, 2021 to Notification of Reasons for Rejection mailed Dec. 22, 2020", w/English Claims, 18 pgs.

"Third party submission filed on Nov. 29, 2017 U.S. Appl. No. 14/865,420", 24 pgs.

"Third-party submission tiled on Dec. 19, 2018 for U.S. Appl. No. 15/747,905", 18 pgs.

"U.S. Appl. No. 17/306,402, Non Final Office Action mailed Aug. 16, 2023", 10 pgs.

"U.S. Appl. No. 17/314,211, Non Final Office Action mailed Aug. 16, 2023", 10 pgs.

"Chinese Application Serial No. 202110174892.7, Office Action mailed Aug. 26, 2023", with machine translation, 8 pgs.

"U.S. Appl. No. 17/306,402, Response filed Nov. 3, 2023 to Non Final Office Action mailed Aug. 16, 2023", 11 pgs.

"U.S. Appl. No. 17/314,211, Response filed Nov. 3, 2023 to Non Final Office Action mailed Aug. 16, 2023", 11 pgs.

"United Kingdom Application Serial No. 2215501.4, Response filed Oct. 23, 2023 to Combined Search and Examination Report mailed Mar. 29, 2023", 13 pgs.

"Chinese Application Serial No. 202110174892.7, Response filed Nov. 29, 2023 to Office Action mailed Aug. 26, 2023", w english claims, 9 pgs.

"United Kingdom Application Serial No. 2215501.4, Subsequent Examination Report under Section 18 (3) mailed Jan. 11, 2024", 3 pgs.

"United Kingdom Application Serial No. 2215501.4, Response filed Feb. 8, 2024 to Subsequent Examination Report under Section 18 (3) mailed Jan. 11, 2024", 6 pgs.

"U.S. Appl. No. 17/314,211, Final Office Action mailed Mar. 13, 2024", 11 pgs.

"U.S. Appl. No. 17/306,402, Final Office Action mailed Mar. 26, 2024", 10 pgs.

"U.S. Appl. No. 17/314,211, Response filed Apr. 23, 2024 to Final Office Action mailed Mar. 13, 2024", 11 pgs.

"U.S. Appl. No. 17/306,402, Response filed May 2, 2024 to Final Office Action mailed Mar. 26, 2024", 12 pgs.

"United Kingdom Application Serial No. 2215501.4, Combined Search and Examination Report mailed Mar. 29, 2023", 8 pgs.

U.S. Appl. No. 14/865,420 U.S. Pat. No. 11,020,166, filed Sep. 25, 2015, Multifunctional Medical Device.

U.S. Appl. No. 15/747,905 U.S. Pat. No. 11,076,909, filed Jan. 26, 2018, Multifunctional Medical Device.

U.S. Appl. No. 17/306,402, filed May 3, 2021, Multifunctional Medical Device.

U.S. Appl. No. 17/314,211, filed May 7, 2021, Multifunctional Medical Device.

"U.S. Appl. No. 17/306,402, Advisory Action mailed Jun. 3, 2024", 3 pgs.

"U.S. Appl. No. 17/314,211, Advisory Action mailed Jun. 3, 2024", 3 pgs.

"U.S. Appl. No. 17/306,402, Response filed Jul. 10, 2024 to Advisory Action mailed Jun. 3, 2024", 8 pgs.

"U.S. Appl. No. 17/314,211, Response filed Jul. 10, 2024 to Advisory Action mailed Jun. 3, 2024", 8 pgs.

"U.S. Appl. No. 17/306,402, Notice of Allowance mailed Aug. 7, 2024", 5 pgs.

"U.S. Appl. No. 17/314,211, Notice of Allowance mailed Aug. 7, 2024", 5 pgs.

"United Kingdom Application Serial No. 2406589.8, First Examination Report Under Section 18(3) mailed Sep. 2, 2024", 5 pgs.

"United Kingdom Application Serial No. 2406589.8, Subsequent Examination Report under Section 18 (3) mailed Apr. 8, 2025", 2 pgs.

"United Kingdom Application Serial No. 2406589.8, Response filed Mar 3, 2025 to First Examination Report Under Section 18(3) mailed Sep. 2, 2024", w claims, 9 pgs.

"United Kingdom Application Serial No. 2406589.8, Response filed Jun. 26, 2025 to Subsequent Examination Report under Section 18 (3) mailed Apr. 8, 2025", w claims, 9 pgs.

(56)        References Cited

OTHER PUBLICATIONS

"United Kingdom Application Serial No. 2406589.8, Subsequent Examination Report mailed Aug. 21, 2025", 4 pgs.
"United Kingdom Application Serial No. 2406589.8, Subsequent Examination Report under Section 18 3 mailed Mar. 24, 2026", 5 pgs.

* cited by examiner

P

NANO SURFACES ON SMOKE PARTICLE ELECTRODES

PRIORITY CLAIM

This application claims the benefit of priority to U.S. Provisional Patent Application No. 63/262,929, filed Oct. 22, 2021, the contents of which are incorporated herein in their entirety.

TECHNICAL FIELD

This document pertains generally, but not by way of limitation, to electrosurgical devices that can be used for various surgical procedures.

BACKGROUND

Electrosurgery uses the application of a high frequency alternating polarity electrical current in combination with mechanical cutting elements such as blades to cut, coagulate, desiccate, or fulgurate tissue. The high frequency alternating current (AC) can be converted to heat by resistance as it passes through tissue. The result of heat buildup within the tissue can be used to cause tissue thermal damage, resulting in effects such as cutting or cautery of tissue. Electrosurgery can allow for high precision cutting in surgery with low blood loss. In some cases, mechanical cutting elements can be used in an alternating fashion or assisted with radio frequency (RF) energy.

SUMMARY OF THE DISCLOSURE

The present disclosure provides apparatus, systems, and methods for smoke management during electrosurgery. A variety of energy devices can be commonly used in surgery for modification of tissue. Such energy devices can include, for example, radio frequency (RF), ultrasonic, cryogenic, and microwave devices. Many of these devices, during use, can cause smoke and obscure vision during a surgical procedure. In some cases, the produced smoke can additionally contain particles that are harmful to the device operator or the patient.

Discussed herein, the use of hydrophobic layers on such energy devices can help reduce smoke production and increase visibility. The hydrophobic layers can include coatings, surface structures, or combinations thereof, that serve as an anti-smoke stick layer on the cutting element. For example, coatings with polysiloxanes or fluorosilanes can be used, or an etched surface providing nano-structures. Optionally, such hydrophobic layers can be used to lubricate the channel in which the cutting element resides.

In an example, an electrosurgical system can include an electrosurgical device, an electrical generator connectable to the device, and a controller coupled to the generator. The device can have a distal portion and a proximal portion. The device can include a longitudinal shaft extending between the distal portion and the proximal portion, the longitudinal shaft configured for at least partial insertion into a patient, a first electrode extending from the longitudinal shaft at the distal portion, a second electrode extending from the longitudinal shaft at the distal portion, wherein the first electrode and the second electrode are of opposing polarities, and a low adhesion layer at least partially covering at least one of the first and second electrodes. The electrical generator can be for providing current to the first electrode and the second electrode. The controller can be configured to adjust an amount of energy applied to the first and second electrodes, such that when in operation a smoke threshold of the low adhesion layer is accounted for. The controller can provide energy up to, but not above the smoke threshold.

In an example, a method can include: inserting an electrosurgical instrument at least partially into a patient, the electrosurgical instrument comprising at least one electrode with a low adhesion layer thereon, and applying a high voltage to the at least one electrode to ionize smoke particles near the target tissue.

In an example, an electrosurgical device can have a distal portion and a proximal portion. The device can include a longitudinal shaft extending between the distal portion and the proximal portion, the longitudinal shaft configured for at least partial insertion into a patient, a first electrode extending from the longitudinal shaft at the distal portion, a second electrode extending from the longitudinal shaft at the distal portion, wherein the first electrode and the second electrode are of opposing polarities, and a hydrophobic layer at least partially covering at least one of the first and second electrodes, the hydrophobic layer configured for uptake of smoke.

In an example, an electrosurgical system can include a bipolar device having a distal portion and a proximal portion, and an electrical generator connectable to the bipolar device. The device can include a longitudinal shaft extending between the distal portion and the proximal portion, the longitudinal shaft configured for at least partial insertion into a patient, a first electrode extending from the longitudinal shaft at the distal portion, a second electrode extending from the longitudinal shaft at the distal portion, wherein the first electrode and the second electrode are of opposing polarities, and a hydrophobic layer at least partially covering at least one of the first and second electrodes, the hydrophobic layer configured for uptake of smoke. The electrical generator can be for providing current to the first and second electrodes.

In an example, a method can include applying a hydrophobic layer to a bipolar electrode on a surgical device, such that the layer at least partially covers the bipolar electrode.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
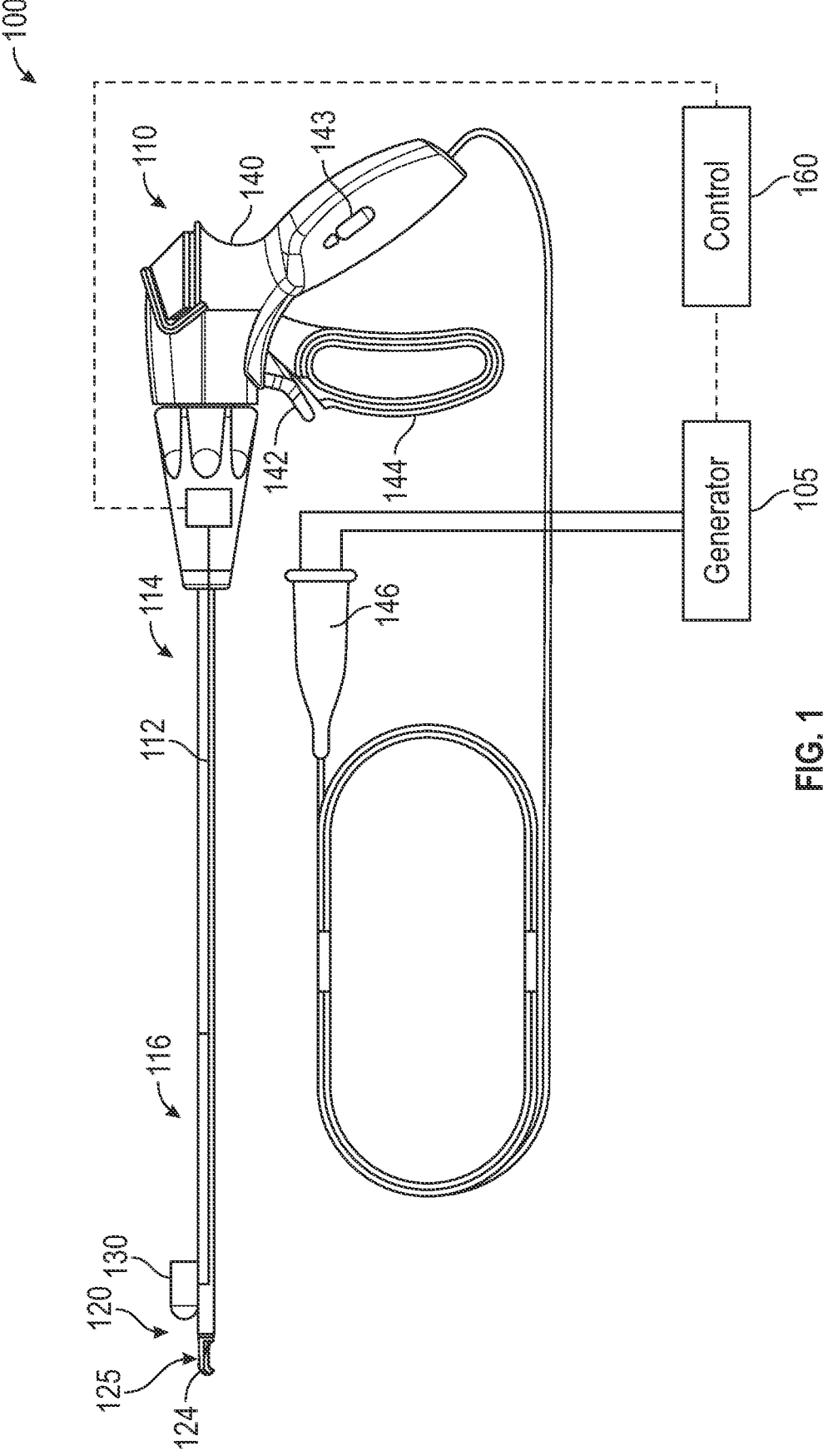
FIG. 1 is a schematic diagram of an electrosurgical system with a bipolar electrode in an example.

Discussed herein are devices and methods for smoke management during electrosurgery. A variety of energy devices can be commonly used in surgery for modification of tissue. Such energy devices can include, for example, radio frequency (RF), ultrasonic, cryogenic, and microwave devices. Many of these devices, during use, can cause smoke and obscure vision during a surgical procedure. In some cases, the produced smoke can additionally contain particles that are harmful to the device operator or the patient.

An DC smoke ionization electrode device can be used to help reduce smoke particles in such electrosurgery methods. Specifically, the use of hydrophobic layers on an DC smoke ionization electrode device can help further reduce smoke production and increase visibility. The hydrophobic layers can include coatings, surface structures, or combinations thereof, that serve as an anti-smoke stick layer on the cutting element. For example, coatings with polysiloxanes or fluorosilanes can be used, or an etched surface providing nanostructures. Optionally, such hydrophobic layers can be used to lubricate the channel in which the cutting element resides.

A hydrophobic layer on the surface of the DC smoke ionization electrode in the smoke reduction device can help prevent the DC smoke ionization electrode from wetting. Specifically, such a layer can help water (or other liquid in the body cavity) pool to particular points on the DC smoke ionization electrode and easily roll off. The prevention of wetting of the DC smoke ionization electrode can help prevent electrode degradation at high voltages, which can help reduce overall smoking.

Additionally, in some cases, the hydrophobic layer can be such that it disperses off the device DC smoke ionization electrode when a sufficiently high voltage is reached. This can help reduce already-produced smoke by ionizing particles between the DC smoke ionization electrode and a second electrode of opposing polarity, such as a pad outside the patient. This can help migrate smoke particles floating in the operation area, such as in the body cavity, to a particular surface, such as on or near the first electrode or a portion of tissue, for later removal. This can help reduce smoke blown into the atmosphere of the operating room.

A system incorporating an electrosurgical device with a DC smoke ionization electrode having a low adhesion (e.g., hydrophobic) layer can also include a controller for directed control of the power supplied to the DC smoke ionization electrode having the hydrophobic layer. For example, the controller can adjust the supply of energy, such as by increasing the voltage supplied to the DC smoke ionization electrode, when the controller is notified that an electrode with a hydrophobic coating (such as is less prone to burning/smoking) is being used. Additionally, the controller can institute a DC circuit with the DC smoke ionization electrode and optionally a second electrode when ionization of smoke particles is desired.

Thus, applying a hydrophobic layer, such as a coating or surface structure, to a smoke reduction device surface can increase the efficacy pf that device to prevent smoking and reduce incidences of obscured vision. In some cases, an etched surface pattern can be used to achieve a hydrophobic effect, instead of a coating, or in combination with a coating.

Smoke particles can be generated during a wide variety of surgical procedures in the body cavity, such as in an insufflated area being operated on. Thermal destruction of tissue often results in a smoke byproduct. This can particularly occur when the electrosurgical instruments are at a high voltage. In such cases, the DC smoke ionization electrode on the anti-smoke device can be subject to wetting and degradation, causing area reduction in efficacy when such an anti-smoke device is used, such as in tandem with another electrosurgical device.

Even in cryosurgery, smoke can form from high voltage surgical electrodes in the form of frozen vapor, droplets, or matter in a fog, suspended in the atmosphere of the room. This smoke and fog can obscure the surgeon's field of view, and can be hazardous. Such smoke particles can obscure the view of a surgeon performing the procedure and may be hazardous to the health of the surgical staff. Many healthcare workers, such as surgeons, nurses, anesthesiologists, and surgical technologist, can be exposed to smoke from laser or electrosurgical procedures. Often, the production of smoke during surgery is referred to as "surgical plume".

Surgical plume can be similar to other types of smoke plumes. Surgical plume can include components such as carbon monoxide, polyaromatic hydrocarbons, and various other toxic gases in trace amounts. Thus, surgical plume can cause a variety of health challenges, such as upper respiratory irritation and in vivo mutagenic potential. Potentially, surgical plume can include infectious viral fragments.

Additionally, production of smoke during a procedure can lead to increased downtime in the operating room, where the patient is under anesthesia for an extended time period. Smoke particles can also potentially foul a camera use in the procedure.

Typical smoke removal methods, such as by vacuum and venting, have been used. These methods can include venting of smoke outside the room and/or filtering smoke particles. In some cases, smoke filters can be used, however, these can be costly. Commonly, the smoke is left to permeate into the operating room during procedures. In some cases, an increase in insufflation gas (i.e., carbon dioxide), can be used to combat smoke. During times of increased tissue modification and higher smoke production, higher insufflation pressure may be desired. Increased pressure of the insufflation gas can sometimes reduce the production of smoke in the body cavity.

For example, in a laparoscopic procedure, gas can be introduced into the patient through access ports to inflate an area of interest in the patient's body. Smoke generated in the insufflated area, for example when diathermic or electrocautery cutting is undertaken, is sucked out and may then be filtered. However, such filters can be expensive, and may not fully filter the smoke particles. Often the smoke is left to permeate into the operating theatre in many procedures, causing undesirable health conditions.

Discussed herein, a low adhesion hydrophobic layer, such as a coating or etched surface, on a surgical instrument, can help reduce and manage smoke produced during surgery.

FIG. 1 illustrates a schematic diagram of an example of portions of an electrosurgery system 100, such as can include an electrosurgery device 110 with an electrosurgical end effector 120 such as a probe using RF energy. The device 110 can be connected to an electrosurgical energy generator 105 and a controller 160. The system 100 can be used for electrosurgery, but may cause smoke evolution. Thus, the use of a separate smoke reduction device in conjunction with the system 100 can be helpful in reducing smoke. For example, the electrosurgery device 110 can be used in a body cavity or surgical site, into which an anti-smoke device can also be inserted and used. If used during surgery, the anti-smoke device can help maintain a field of vision for the surgeon using the electrosurgery device 110.

The electrosurgery device 110 can include a longitudinal shaft 112 having a proximal portion 114 and a distal portion 116. The distal portion 116 can include an end effector 120 with a low adhesion low adhesion layer 225. A proximal portion 114 of the device can be connected to a handpiece 140, such as with actuators 142, 143, and 144. The device 110 can also include a connector 146 such as can be configured to be connected to the generator 105.

The generator 105 can be external to but coupled to the electrosurgical device 110. The generator 105 can provide electrical energy to the end effector 120 of the electrosurgical device 110, such as through the electrical connector 146. The electrical generator 105 can produce a current deliverable by the end effector 120 such as for inducing a coagulation mode of electrosurgery. The electrical generator 105 can be in communication with the controller 160, which can direct the application of electrosurgical energy to the end effector 120 in the electrosurgical device 110.

The type and amount of electrical energy provided by the generator 105 can vary, such as depending on the desired treatment. The electrosurgical waveform produced, the voltage, and the power of the electrosurgical energy being delivered, and the size and surface area of the end effector 120, can affect the depth and the rate of producing heat, which, in turn, can alter the final effect on the target tissue.

The electrosurgery device 110 can include a bipolar electrosurgery end effector 120 such as for applying high-frequency alternating polarity electrical current to biological tissue, such as to cut, coagulate, desiccate, or fulgurate the tissue, such as may be desired by the surgeon treating the patient. The electrosurgery device 110 can include a wet field device such as for wet field electrosurgery, such as in a saline solution, or in an open wound. In a wet field device, heating can result from an AC current passing between two electrodes. Heating can be the greatest where the current density is the highest. Thus, smaller surface area electrode can produce a greater amount of heat for treating tissue.

In the device 110, the shaft 112 with the proximal portion 114 and the distal portion 116 can be sized, shaped, or arranged for partial insertion of the device 110 into a patient. The shaft 112 can include or can be made of one or more of a composite, plastic, or metallic material, or other material suitable for surgical applications. The proximal portion 114 can be near an operator, such as a surgeon, when the device 110 is in use. In some cases, the operator can be a robotic arm or other machine. The distal portion 116 can be sized, shaped, or arranged for insertion into the patient so that distal portion 116 is further from the operator during use.

In some cases, the shaft 112 can be sized, shaped, arranged, or otherwise configured for laparoscopy, in some cases, the shaft 112 can be shorter such as for open surgery applications. In some cases, such as for laparoscopy, the shaft can be long. In an open surgery application, the shaft can include a tissue interface element with cutting, coagulating, and sensing elements in or on a distal portion of that device.

The end effector 120 can be located at or near the distal portion 116 of the shaft 112. The end effector 120 can include a bipolar electrode such as for use in coagulating tissue. Bipolar electrodes can make use of high frequency electrical current such as to cut, coagulate, desiccate, or fulgurate tissue. With a bipolar electrode configuration, current passes through the tissue between two more closely-spaced electrodes, such as between individual electrode arms of a forceps-type electrode. In a bipolar configuration, the current passes through the tissue between tips of two active electrodes, such as between electrode tips of a bipolar forceps. The electrical generator 105 can be connected to both active and return electrodes, such as for sending and receiving current. The end effector 120 can be configured to heat the targeted tissue.

The handpiece 140 can include one or more user-actuators, such as the actuators, 143, 144. In some cases, these can include one or more of levers, buttons, wheels, switches, triggers, or a combination thereof. One of the actuators 142, 143, 144, can provide a user-interface to control a first switch that selectively connects the end effector 120 to the generator 105 or other circuitry that can provide electrosurgical energy to the first end effector 120 such as for cutting and coagulation. Additional actuators, such as buttons, triggers, or other user-actuatable mechanisms can be included on the handpiece 140 of the device 110 or elsewhere for surgeon use, such as for direction and action of the end effector 120, movement of the shaft 112, or one or more other operations of the device 110.

The electrosurgical device 110, including the triggers on the handpiece 140, the end effector 120, and the one or more sensors 130, can be in communication with the controller 160. The generator 105 can also be in communication with the controller 160. The controller 160 can include a processor and a memory such as to permit the controller 160 to communicate with and control the generator 105. The controller 160 can be used to allow for both predictive and reactive control of the duty cycle produced by the generator 105.

The controller 160 can operate as a standalone device, or may be networked to other machines. The controller 160 can be configured to regulate the generator 105 and produce different voltages of energy to the electrodes on the end effector 120. The low adhesion low adhesion layer 225 can help protect the electrodes on the end effector 120, such as by allowing for the electrodes to receive relatively higher voltage without burning. Thus, the electrodes are less likely to degrade/burn and smoke. The controller 160 can recognize the electrodes with the low adhesion layer, and adjust the voltage up when such coated electrodes are being used.

In some cases, the controller 160 can be configured to produce an application of DC current to the electrodes such as to ionize particles, such as smoke particles, between the electrodes. In this case, the run-off of water from the low adhesion low adhesion layer 225 on the electrodes can help clean the electrodes and allow for high efficacy of ionization. Overall, the controller 160 can be programmed to adjust the supply of energy to the end effector 120 based on the low adhesion low adhesion layer 225.

The controller 160 can include a hardware processor, such as a central processing unit (CPU), a graphics processing unit (GPU), a hardware processor core, or any combinations thereof. The controller 160 can further include a memory, including a main memory and a static memory. The controller 160 can include an input device, such as a keyboard, a user interface, and a navigation device such as a mouse or touchscreen.

The controller 160 can additionally include a storage device, a signal generation device, a network interface device, and one or more sensors. The storage device can include a machine readable medium on which is stored one or more sets of data structure or instructions embodying or utilized by any one or more of the techniques described herein. The instructions may also reside, completely or at least partially, within the main memory, within static memory, or within the hardware processor during execution thereof by the controller.

In an example, one or any combination of the hardware processor, the main memory, the static memory, or the storage device may constitute machine readable media, that may include any medium that is capable of storing, encoding, or carrying instructions for execution by the controller 160 and that cause the controller 160 to perform any one or more of the techniques of the present disclosure, or that is capable of storing, encoding or carrying data structures used by or associated with such instructions. Non-limiting machine readable medium examples may include solid-state memories, and optical and magnetic media. The instructions on the controller 160 may further be transmitted or received over a communications network using a transmission medium via a network interface device.

Various electrosurgical waveforms can be used for electrosurgical procedures. Rapid heating of tissue using a continuous waveform can result in vaporization, fragmentation, and ejection of tissue fragments, allowing for tissue cutting. Open circuit voltage of such electrical waveforms can be, for example, from about 300 to about 10,000 V peak-to-peak, inclusive.

Shown in FIG. 1, the end effector 120 can be a surgical cutting device, such as a J-hook type bipolar device, a probe, a jaw, or other RF type cutting devices. In other cases, the device can be another bipolar cutting instrument that might produce smoke on or near the cutting end of the device.

As tissue is modified, such as with the device 110, smoke can be produced during surgery, such as by or near the use of the end effector 120.

Thus, the system 100 can further include an anti-smoke device 200 with a low adhesion low adhesion layer 225. Referring now to FIG. 2, the device 200 can be a device containing at least one DC smoke ionization electrode 220. The DC smoke ionization electrode can be coupled to a DC voltage source. For example, the generator 105 can additionally provide a DC voltage to the device 200. Alternatively, a separate DC voltage source can be used and coupled to the DC smoke ionization electrode 220. This can allow provision of an ionizing DC voltage to the surgical site where the device 110 is being used. The DC smoke ionization electrode 220 can be positionable with the patient on, near, or in the surgical site. When an ionizing DC voltage is applied to the DC smoke ionization electrode 220, smoke particles located at the DC smoke ionization electrode 220 can be ionized. In some cases, a second electrode, such as a pad outside the patient, can be used in conjunction with the device 200. The DC smoke ionization electrode 220 can be configured to disperse and ionize nearby smoke particles when exposed to a voltage above a specific threshold.

The low adhesion low adhesion layer 225 can, for example, be a superhydrophobic layer for preservation of the anti-smoke device 200 being used to reduce smoke in the surgical area. The low adhesion layer 225 can have a surface energy less than that of an underlying portion of the DC smoke ionization electrode 220. The low adhesion layer 225 can have a contact angle such that water (or other liquid) on or near the electrodes of the end effector 120 can pool on the surface of the electrodes at particular areas. The pooling of water on low adhesion layer 225 can allow for uneven dispersion of electrons on the surface of the electrodes. This can help create various current densities that improve ionization of nearby particles. In this way, the low adhesion layer 225 can inhibit wetting of the DC smoke ionization electrode 220.

In some cases, low adhesion low adhesion layer 225 can be a coating, such as polydimethylsiloxane, hexadimethylsiloxane, or tetramethyldisiloxane. In an example, low adhesion low adhesion layer 225 can have a thickness in range of about 10 nm to about 300 nm. In some cases, low adhesion low adhesion layer 225 can have a substantially uniform thickness. In some cases, low adhesion low adhesion layer 225 can have a non-uniform thickness. In some cases, low adhesion low adhesion layer 225 can be discontinuous. In some cases, the anti-smoke layer can be continuous. Low adhesion low adhesion layer 225 can include one or more asperities, such as nanoparticles. Low adhesion low adhesion layer 225 can include an electrically insulated or a non-conductive material. In some cases, low adhesion layer 125 can include a hydrophobic surface structure, a coating, or a combination thereof. In some cases, low adhesion low adhesion layer 225 can overlap a portion of the electrode 124.

The low adhesion layer 225 can help reduce smoke created during electrosurgery, and help reduce surgical plume. The low adhesion layer 225 can be hydrophobic or superhydrophobic. This can help prevent the electrodes on the end effector 120 from being wetted during operation. This can reduce degradation and subsequently smoking of the surgical electrodes. Additionally, the hydrophobicity of the low adhesion layer 225 can help absorb smoke that is produced during surgery.

This low adhesion layer 225 can be chosen and applied to the end effector 120 of the end effector 120 to prevent or reduce sticking of tissue to the end effector 120 of the device 110 and prevent carbonization of the insulative material. Low adhesion layer 125 can, for example, include a nanostructure and a non-stick structure to reduce sticking of the coagulum to the tip of the device 110. Low adhesion low adhesion layer 225 can, for example, have a low surface energy, such as to prevent sticking of coagulum to the device. Low adhesion low adhesion layer 225 can allow for reduction of thermal transfer between the end effector 120 and the target tissue, so as to reduce smoking of the target tissue during surgery. In some cases, low adhesion low adhesion layer 225 can include super hydrophobic materials.

The end effector 120 can extend distally from the shaft. The end effector 120 can include electrode 124, along with low adhesion layer 225. The end effector 120 can be used, for example, for surgery such as colon surgery or intestinal surgery. The end effector 120 can be used for modifying tissue, such as by cutting or coagulation. The end effector 120 can further include the low adhesion low adhesion layer 225.

In an example, the low adhesion layer 225 can include a non-electrically conductive coating on an external surface of the end effector 120, or an insulative coating. The low adhesion layer 225 can have a resistance or impedance of less than about 10 ohms, or less than about 5 ohms. The low adhesion layer 225 can have a surface adherence less than that of the electrode 124. The low adhesion layer 225 can, for example, have a coefficient of friction that is lower than that of the cutting element 123.

In some cases, the coating can be uniform in coverage and thickness, in some cases it can be fully or partially coating the end effector 120. The low adhesion layer 225 can have a thickness of up to about 300 nm, up to about 200 nm, up to about 100 nm, or less. In some cases, the low adhesion layer 225 can be hydrophobic or superhydrophobic. In some cases, the low adhesion layer 225 can have a nanostructure or microstructure to reduce smoke.

Examples of the present disclosure provide for disposing a non-stick coating on components of an electrosurgical device at a particular thickness or within a particular range of thicknesses such that the non-stick coating provides adequate tissue sticking reduction during tissue sealing without negatively impacting tissue sealing performance of the device.

As discussed herein, a thickness of low adhesion low adhesion layer 225 can be in the range of 10 nm to about 300 nm and provide non-stick benefits. However, while hydrophobic properties can be provided, various portions of this range can provide additional benefits, while still providing tissue adhesion resistance and sensing capability. In one example, the non-stick coating can be a thin coating, e.g. having a thickness in the range of, but not limited to, about 10 nm to about 30 nm. In one example, the non-stick coating has a thickness in the range of about 10 nm to about 20 nm. In one example, the non-stick coating has a thickness less than 20 nm such as about 15 nm.

Low adhesion low adhesion layer 225 can allow passage of energy, such as RF energy, through such that the end effector 120 can affect the target tissue. For example, the low adhesion layer 225 can be a light capacitive element or light resistive element, that allows passage of electrode energy through the low adhesion layer 225. The low adhesion layer 225 can be directly applied to the cutting element 123 and the electrode 124. In some cases, an adhesive can be used to apply the low adhesion layer 225 to the device 110.

As discussed herein, the non-stick coating can be applied to portions of the electrosurgical device to provide smoke filtering and removal properties. Any material capable of providing the desired functionality, such as reduction of smoke while simultaneously maintaining sufficient electrical transmission to permit tissue sealing, may be used as the non-stick layer, provided it has adequate biocompatibility. In some examples, the material may be porous to allow for electrical transmission.

In some cases, the low adhesion layer 225 can include a polymeric-based coating, such as a fluoropolymer type coating. In some cases, the low adhesion layer 225 can include a Polytetrafluoroethylene (PTFE) coating. In some cases, the low adhesion layer 225 can include a polysiloxane or a fluorosilane coating. For example, materials such as silicone and silicone resins can be used for the non-stick coating. In one example, the silicone and silicone resins can be applied using a plasma deposition process to precisely control thickness, and can withstand the heat generated during tissue sealing. Silicone resins suitable for the non-stick coating include, but are not limited to, polydimethyl siloxanes, polyester-modified methylphenyl polysiloxanes, such as polymethylsilane and polymethylsiloxane, and hydroxyl functional silicone resins. In some examples, the non-stick coating is made from a composition including a siloxane, which may include hexamethyldisiloxane, tetramethylsilane, hexamethyldisilazane, or combinations thereof.

In an example, the coating is a polydimethylsiloxane ("PMDSO" coating. In one example, the coating is a hexamethyldisiloxane ("HMDSO") coating. In another example, the coating is a tetramethyldisiloxane (TMDSO or TMDS). In some cases, the low adhesion layer 225 can include a thin layer of hexamethyldisiloxane (HMDSO), of a thickness of a few nano meters. HMDSO is electrically resistive, but the thinness of the coating can allow passage of RF energy therethrough.

The application of the anti-smoke layer may be accomplished using any system and process capable of precisely controlling the thickness of the coating. In some examples, HMDSO is deposited on the electrically conductive sealing plates using plasma enhanced chemical vapor deposition (PECVD) or other suitable methods such as atmospheric pressure plasma enhanced chemical vapor deposition (AP-PECVD). For example, the application of the polydimethylsiloxane coating may be accomplished using a system and process that includes a plasma device coupled to a power source, a source of liquid and/or gas ionizable media (e.g., oxygen), a pump, and a vacuum chamber. The power source may include any suitable components for delivering power or matching impedance to the plasma device. More particularly, the power source may be any radio frequency generator or other suitable power source capable of producing electrical power to ignite and sustain the ionizable media to generate a plasma effluent. Application of the coating is discussed in more detail below with reference to FIG. 6.

In some cases, low adhesion low adhesion layer 225 can include an etched coating including one or more hydrophobic pillars superimposed on the electrode 124. With an etched low adhesion layer 225, a nanostructure of hydrophobic pillars can act as a superhydrophobic layer with a low surface energy, reducing sticking. The etched low adhesion layer 225 can be in any suitable pattern for the non-stick coating to reduce or prevent tissue sticking. The etched low adhesion layer 225 can be applied, for example, by printing, chemical etching, laser etching, chemical bombardment, or other suitable techniques. Application of the coating is discussed in more detail below with reference to FIGS. 3-8.

In some cases, it may be beneficial to have different hydrophobic physical structures on different surfaces of components of the device. The hydrophobic physical structure may be on all or a portion of a surface of the device 110, and different hydrophobic physical structures may be used on different surfaces or components of a device. Example hydrophobic structures are discussed below in FIGS. 3-5.

Figure 2A:
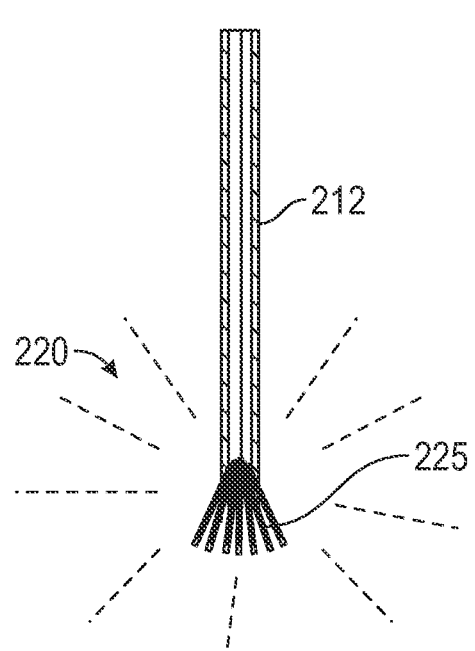
FIGS. 2A-2C are schematic diagrams of a bipolar surgical device in an example.
Figure 2B:
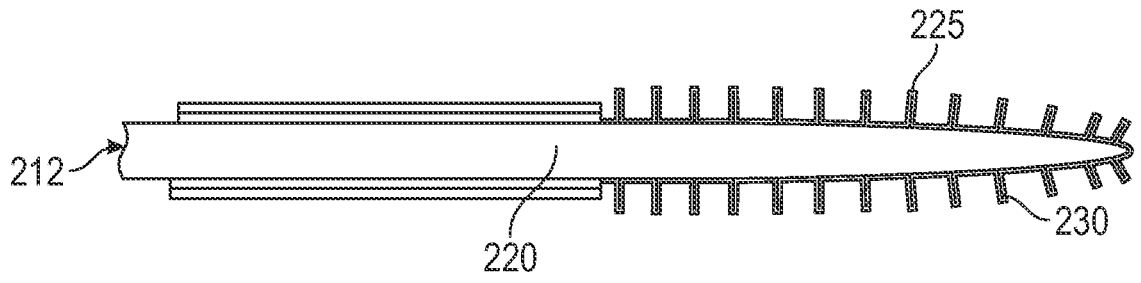
Figure 2C:
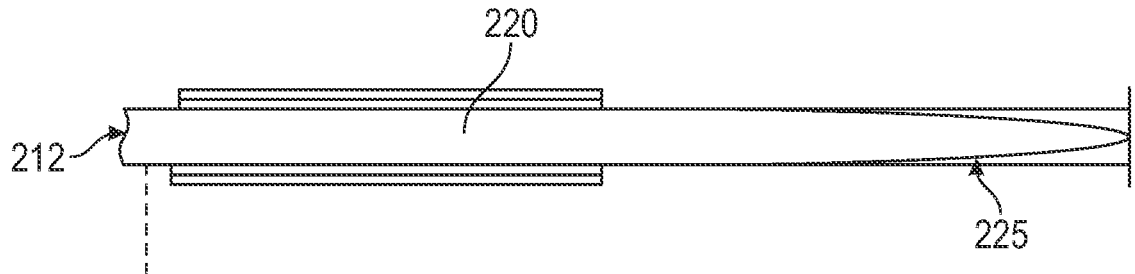

FIGS. 2A-2C are schematic diagrams of a bipolar surgical device 200 in an example. The device 200 can include DC smoke ionization electrode 220 extending from a longitudinal shaft 212 on a distal portion 216. The DC smoke ionization electrode 220 can further include a low adhesion layer 225. As tissue is modified, such as with the device 200, smoke can be produced during surgery. Thus, the DC smoke ionization electrode 220 can further include a low adhesion layer 225.

The device 200 in FIGS. 2A-2C can have the low adhesion layer 225. The low adhesion layer 225 can help prevent wetting of the electrodes in the end effector, reducing electrode degradation and smoking. Additionally, when a high voltage is applied to the device 200, the low adhesion layer 225 on the DC smoke ionization electrode 220 can partially disperse liquids and improve ionization efficacy to help reduce smoke already produced in the body cavity. Specifically, the hydrophobic low adhesion layer 225 can induce this behavior.

In some cases, the low adhesion layer 225 can have an impedance of less than about 10 Ohms. In some cases, the low adhesion layer 225 can have a coefficient of friction of about 0.05 to about 0.15. In some cases, the low adhesion layer 225 can include a superhydrophobic layer having a plurality of Nidus points. In some cases, the low adhesion layer 225 can include hydrophobic pillars.

On DC smoke ionization electrode 220 and the layer 225, liquid or water can attempt to form. The layer 225 can be superhydrophobic, such that the water pools in particular areas along the surface of the layer 225. For example, the layer 225 can be in a Cassie state. The contact angle hysteresis can be very low for the layer 225 to allow the pooling at focus points or nidus points. The Cassis state and nidus points are discussed in more detail below. The formation of such nidus points can allow for formation of current density around each of those nidus points. The current density at those points can improve the ability of the coated electrode material to pass electrons for positive and negative charges. When a DC circuit is formed between the electrodes in the DC smoke ionization electrode 220 and a generator (e.g., generator 105 discussed above), the electrical potential between the electrodes can more effectively ionize nearby smoke particles, driving them towards one of the electrodes and out of the air.

In device 200, the DC smoke ionization electrode 220 can be, for example, a bipolar surgical device, such as with first and second electrodes of opposite polarity. The device 200 can be connected to a generator (such as discussed with reference to FIG. 1) that can provide high voltage DC electricity. The first and second electrodes can be in connection with the generator and form a DC circuit that can ionize, reduce, and remove smoke particles generated onsite at the target tissue during surgery.

The DC smoke ionization electrode 220 can include the hydrophobic low adhesion layer 225. The low adhesion layer 225 can be situated in at least one of the electrodes. In some cases, nano technology surface treatments can be used to form the low adhesion layer 225. The low adhesion layer 225 can be a superhydrophobic surface, such as through modification of the structure of the surface of the electrodes. In an example, such surface modifications can be made through laser etching hydrophobic pillars.

The hydrophobic low adhesion layer 225 can prevent wetting and deterioration of the electrostatic capabilities of the electrodes on the DC smoke ionization electrode 220. This can help prevent production of smoke from the DC smoke ionization electrode 220 during operation but preventing the electrodes themselves from smoking.

In FIG. 2B, the DC smoke ionization electrode 220 can include extension 230. Each of the extensions 230 can be fully or partially covered with the low adhesion layer 225. In FIG. 2C, the DC smoke ionization electrode 220 can be a smooth probe tip. The probe tip can be fully or partially covered with the low adhesion layer 225.

A variety of combinations or types of patterning, coating, or other hydrophobic surface structures can be used for the low adhesion layer 225. For example, all of the surfaces of the first and second electrodes can be covered with the low adhesion layer 225. In some cases, selected areas of the first and second electrodes can be covered with the low adhesion layer 225. For example, selective patternation can be done to surface-modify only a portion of each electrode surface. In some cases, chemical etching can be used. In some cases, deposition of a hydrophobic material, such as HMDSO, can be used at a thickness that still allows for movement of electrical energy for surgical application.

In some cases, material deposited on the surface of the first and or second electrode surfaces (e.g., such as a nano surface material or other hydrophobic material) can be combined with an electrical conduction material, such as silver particles, to enhance the electrical conductivity of the layer.

The low adhesion layer 225 can have a superhydrophobic surface co-efficient and also demonstrates a low contact angle hysteresis. For instance, the low adhesion layer 225 can have a contact angle greater than about 100°.

The nano coatings or surface modifications of the anti-smoke layer 225 can be non-hierarchical. A non-hierarchical structure can provide a significant benefit, as condensation does not build on non-hierarchical structures. Additionally, performance efficiency can be expected from the surface modification, such as in versions containing conductive elements and those of the base electrode material. In this case, the Hydrophobic pillars can provide an improvement in device efficiency as they provide 'nidus points' for the ions to focus and release from.

Figure 3:
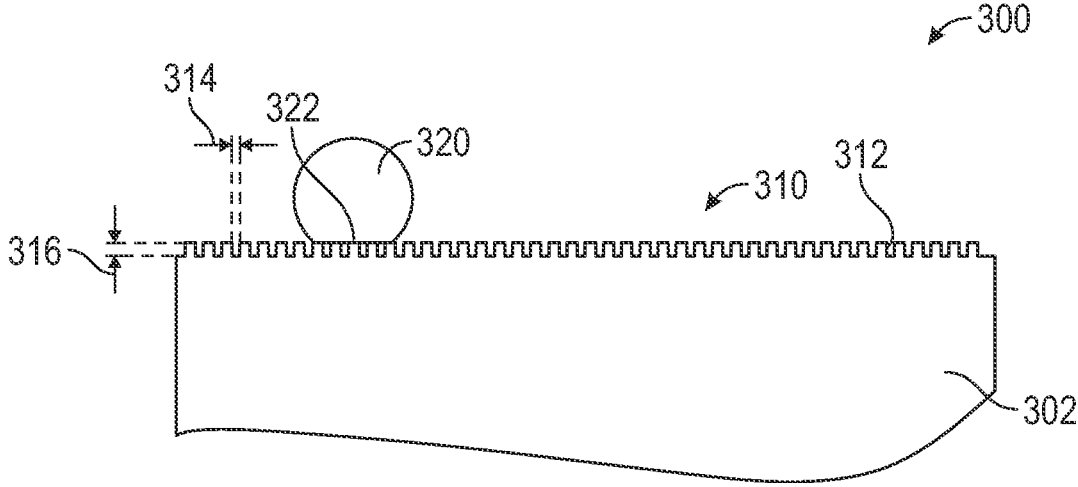
FIG. 3 depicts a schematic diagram of a surface on a surgical device coating with a hydrophobic layer in an example.
Figure 4:
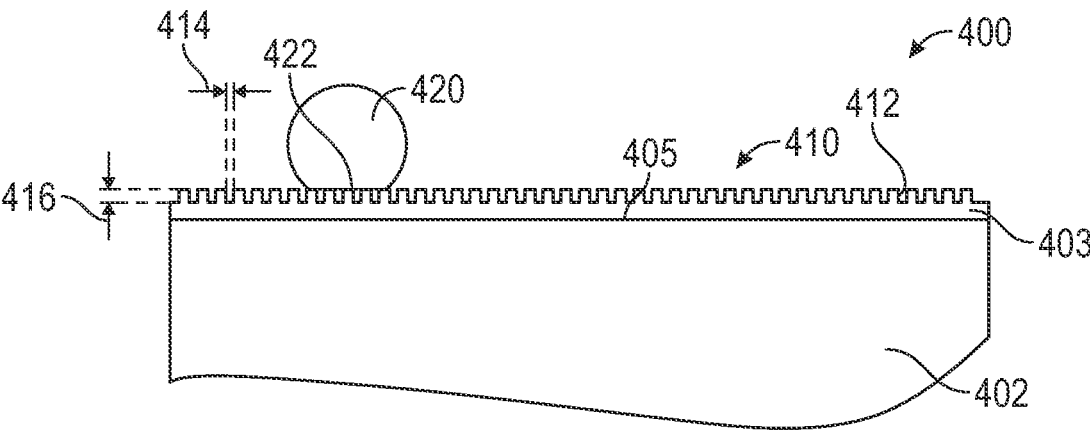
FIG. 4 depicts a schematic diagram of a surface on a surgical device coating with a hydrophobic layer in an example.
Figure 5:
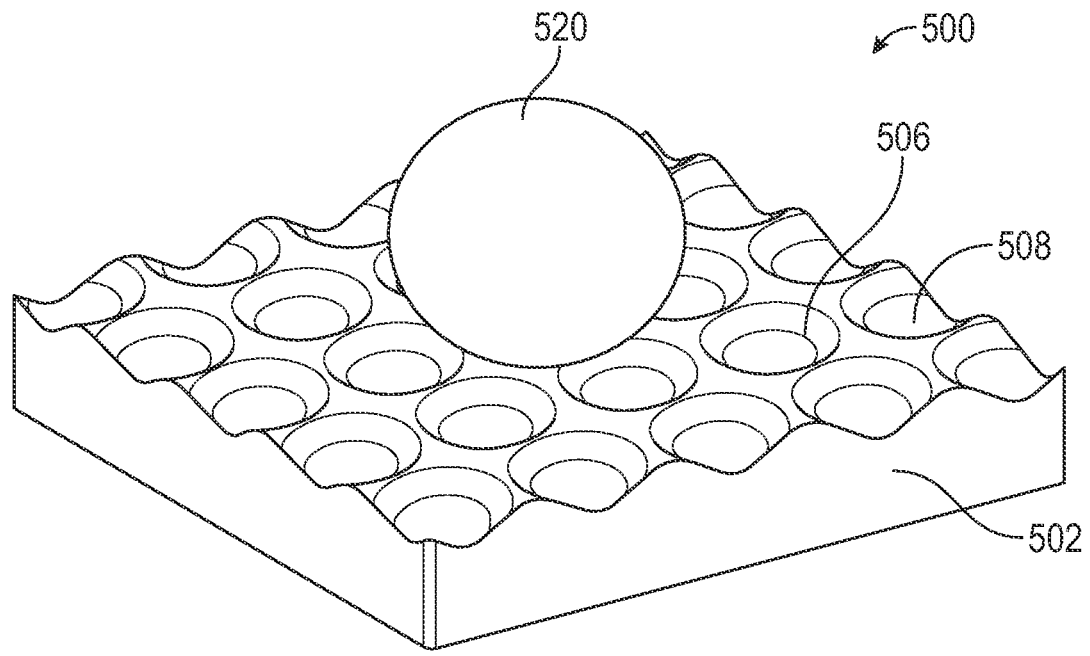
FIG. 5 depicts a schematic diagram of a surface on a surgical device coating with a hydrophobic layer in an example.

FIGS. 3-5 depict schematic diagrams of various examples of an anti-smoke layer that can be used on elements of electrosurgery cutting device end effectors.

FIG. 3 is a schematic diagram of a surface on a surgical device coating with a hydrophobic layer in an example. FIG. 3 shows one example of a surface with a hydrophobic physical structure 310 on a substrate 302 As discussed in examples above, the hydrophobic physical structure 310 may be on all or a portion of a surface, and different hydrophobic physical structures 310 may be used on different surfaces or components of an electrosurgical cutting device. For example, the hydrophobic physical structure 310 may be on elements of a cutting device end effector. The hydrophobic physical structure 310 may be on only a portion the end effector.

As shown in FIG. 3, in one example, the hydrophobic physical structure 310 includes asperities 312 having a height 316 and a pitch 314. The hydrophobic physical structure 310 can be described by the following equation:

$$\Lambda_C = \frac{-\rho g V^{1/3}\left(\left(\frac{1-\cos(\theta_a)}{\sin(\theta_a)}\right)\left(3+\left(\frac{1-\cos(\theta_a)}{\sin(\theta_a)}\right)^2\right)\right)^{2/3}}{(36\pi)^{1/3}\gamma\cos(\theta_{a,0}+w-90)}$$

where $\Lambda$ is a contact line density, and $\Lambda c$ is a critical contact line density; $\rho$=density of the liquid droplet; g=acceleration due to gravity; V=volume of the liquid droplet; $\theta a$=advancing apparent contact angle; $\theta a,0$=advancing contact angle of a smooth substrate; $\gamma$=surface tension of the liquid; and w=tower wall angle.

The contact line density $\Lambda$ is defined as a total perimeter of asperities over a given unit area.

In one example, if $\Lambda > \Lambda c$ then a droplet 320 of liquid are suspended in a Cassie-Baxter state. Otherwise, the droplet 320 will collapse into a Wenzel state. In one example when a Cassie-Baxter state is formed, an ultra-hydrophobic condition exists, and a low adhesion surface is formed. FIG. 3 illustrates a Cassie-Baxter state, where the droplet 320 rests on top of the asperities 312 at interface 322. Although rectangular asperities are shown for illustration purposes, the invention is not so limited. Asperity shapes are considered in the formula above, at least in the tower wall angle (w) term.

In the example of FIG. 3, the asperities are formed directly from a bulk material, and are not formed from a separate coating. One method of forming asperities directly from a bulk material includes chemical etching. Another example of forming asperities directly from a bulk material includes laser etching or ablation. Another example of forming asperities directly from a bulk material includes ion etching.

FIG. 4 shows another example of a surface with a hydrophobic physical structure 410 on a substrate 402. As discussed in examples above, the hydrophobic physical structure 410 may be on all or a portion of a surface, and different hydrophobic physical structures 410 may be used on different surfaces or components of an endoscope. For example, the hydrophobic physical structure 410 may be on an entire outer surface of an end effector. The hydrophobic physical structure 410 may be on only a portion of an outer surface of an end effector.

As shown in FIG. 4, in one example, the hydrophobic physical structure 410 includes asperities 412 having a height 416 and a pitch 414. However, in the example of FIG. 4, the hydrophobic physical structure 410 is formed as part of a coating 403 that forms a direct interface 405 with substrate 402. FIG. 4 illustrates a Cassie-Baxter state, where the droplet 420 rests on top of the asperities 412 at interface 422.

In one example, the asperities 412 are formed by application of nanoparticles to a surface of the substrate 402 to form the coating 403. In one example, the asperities 412 are formed by application of nanoparticles to a surface of the coating 403. In one example, the nanoparticles include hexamethyldisiloxane (HMDSO) particles. In one example, the nanoparticles include tetramethyldisiloxane (TMDSO) particles. In one example, the nanoparticles include fluorosilane particles. Other nanoparticle materials are also within the scope of the invention. In one example, a hydrophobic chemistry of the nanoparticle, in combination with a nano scale asperity structure as shown in FIG. 4 provide better hydrophobicity compared to a hydrophobic chemistry alone.

FIG. 5 shows one example of a laser etched surface 500 that includes hydrophobic physical structure as described above. In the example of FIG. 5, a gaussian hole array is formed by applying laser energy to a surface of a substrate 502 in a controlled regular pattern to form holes 506. A shape of the holes 506 is characterized as gaussian due to the energy distribution of laser energy in forming the array. In the example shown, a number of asperities 508 are formed in the process that may be spaced and arranged in an array that provides a Cassie-Baxter state as described above. A liquid droplet 520 is illustrated on the hydrophobic physical structure similar to the droplet from FIG. 3, or the droplet from FIG. 4.

Figure 6:
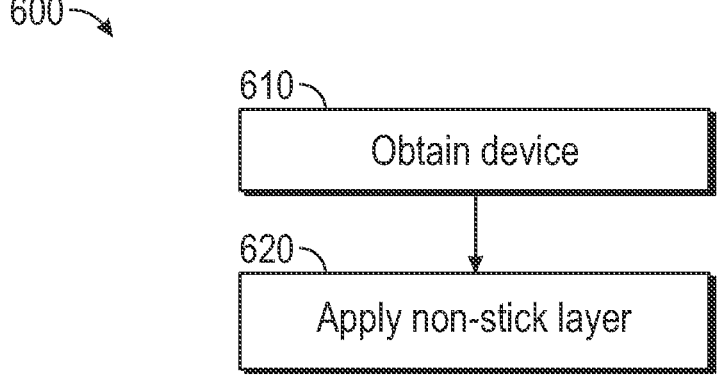
FIG. 6 depicts a flow chart depicting a method of making a hydrophobic surface structure on a bipolar electrosurgical device, in an example.

FIG. 6 is a flow chart depicting a method 600 of applying a hydrophobic layer to a surgical device. The method 600 can include obtaining an electrosurgery cutting device (block 610) and applying an anti-smoke layer (block 620).

The method 600 can include coating or etching the surface of cutting elements of a bipolar cutting device with a non-stick layer, such that the layer at least partially covers the cutting element. Application of the coating or layer can be done, for example, by chemical etching, laser etching, chemical bombardment, or printing.

In some cases, the coating can be produced in a uniform thickness of about 1 nm to about 300 nm, of about 5 nm to about 200 nm, or of about 10 nm to about 100 nm. In some cases, the coating can be produced in a pattern, such as to create hydrophobic pillars on the electrode. In some cases, the coating can fully or partially cover the electrode.

Several modification/application techniques may be used to form the coating, optionally including hydrophobic pillars. In one example, a sol-gel process can be used. Advantages of sol-gel application include the ability to coat more complex surfaces with high quality films. Challenges of sol-gel may include brittleness, limited thickness options, and induced mechanical stresses in the coating.

In one example, a cold spray process can be used. Advantages of cold spray application include the ability to coat at lower temperatures, with low deterioration, low oxidation, and low defects. Challenges of cold spray may include high energy needed for application, high cost, and a limited number of compatible substrates.

In one example, a chemical vapor deposition (CVD) process can be used. Advantages of CVD application include a high quality coating, high control of thickness, and the ability to coat complex surfaces. Challenges of CVD may include high temperature requirements, and high cost.

In one example, a physical vapor deposition (PVD) process can be used. Advantages of PVD application include the ability to coat inorganic compounds, ecological friendly processes, and a wide variety of available coating materials. Challenges of PVD may include high vacuum chamber requirements and high cost.

In one example, a thermal spray process can be used. Advantages of thermal spray application include a large selection of compatible coating materials and substrate materials, and low cost. Challenges of thermal spray may include difficulty in forming thick coatings, low adhesion issues of coatings, and ecologically unfriendly process steps.

In one example, an in-situ polymerization process can be used. Advantages of in-situ polymerization include the ability to coat with insoluble polymers. Challenges of in-situ polymerization may include process complexity, high cost, and limited potential for large scale production.

In one example, a spin coating process can be used. Advantages of spin coating include high quality coatings, fast drying times, and controllable thicknesses. Challenges of spin coating may include difficulty coating small surfaces and requirements of a smooth surface.

In one example, a dip coating process can be used. Advantages of dip coating include the ability to coat complex surfaces and the ability for large scale production. Challenges of dip coating may include undesirable solvent requirements, and limitations of only soluble polymer coatings.

In one example, an electrodeposition process can be used. Advantages of electrodeposition include high quality coatings at low cost. Challenges of electrodeposition may include long process times, and conductive substrate requirements.

Medical devices having a coating optionally including hydrophobic pillars as described show reduced adhesion over other non-textured coatings for bio-materials including, but not limited to, tissues, blood, fats, and/or other biological materials. Application of hydrophobic physical structures to other surfaces of medical devices apart from optical components may further provide advantages such as reduced friction and reduced adhesion where desired.

FIGS. 7A-7D show four different examples of regular periodic physical structure formed on a surface, such as a coating surface, or a surface of a bulk material. Physical dimensions of the regular periodic physical structure dictate different states of interaction with a liquid, such as water, or other fluids. One of ordinary skill in the art, having the benefit of the present disclosure, will recognize that the variable of surface tension $\gamma$ as used in the equation above, is at least partially determined by material properties such as surface energy, and that a surface condition as shown in FIGS. 7A-7D depends in part on a choice of material in both a substrate and a liquid medium.

Figure 7A:
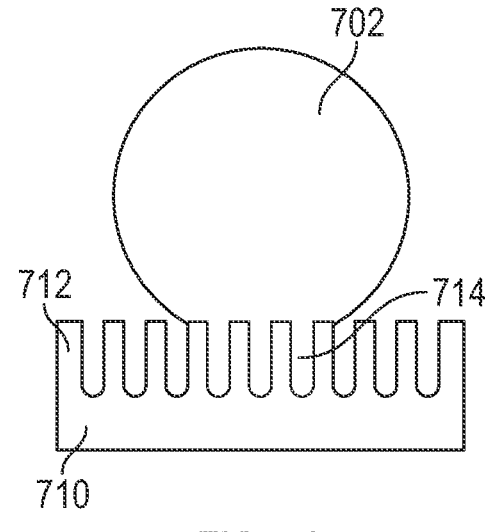
FIGS. 7A-7D depicts examples of regular periodic physical structure formed on a surface, such as a coating surface, or a surface of a bulk material.

FIG. 7A shows a Wentzel state of interaction. A substrate 710 and a liquid medium 702 in a droplet form are shown. The substrate 710 includes a plurality of asperities 712 that are regularly spaced and define a number of spaces 714 between asperities 712. The substrate 710, asperities 712, and spaces 714 can be characterized by the equation above.

Figure 7B:
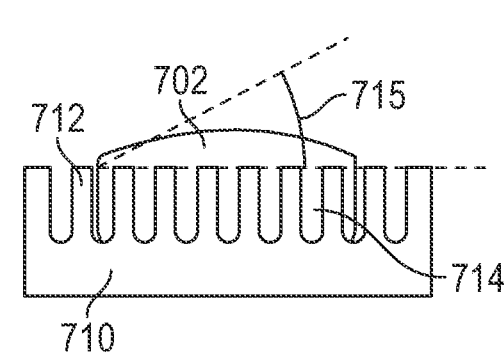

In FIG. 7A, the asperities 712 define a contact line density $\Lambda$ that is less than the critical contact line density $\Lambda c$. As such, in FIG. 7A, a portion of the liquid medium 702 penetrates into the spaces 714 between asperities 712 in the regular periodic physical structure. FIG. 7B shows a hydrophilic Wentzel state where a contact angle 715 is less than 90 degrees. In one example, the superhydrophilic state is defined by a contact angle 715 less than 10 degrees. In lower contact angle states, the water or other fluid on and within the regular periodic physical structure facilitates fast dispersal of any additional fluid or contaminant that may come into contact with the surface. In a surgical context, material such as blood, tissue, etc. will be more easily flushed from a surface due the water within the hydrophilic regular periodic physical structure providing a lubrication or material transport effect. In a more preferred example, the superhydrophilic state is defined by a contact angle 715 less than 5 degrees. The lower contact angle provides lower resistance to lateral movement across the surface of material such as blood or tissue that is desired to be cleared from a local region.

Figure 7C:
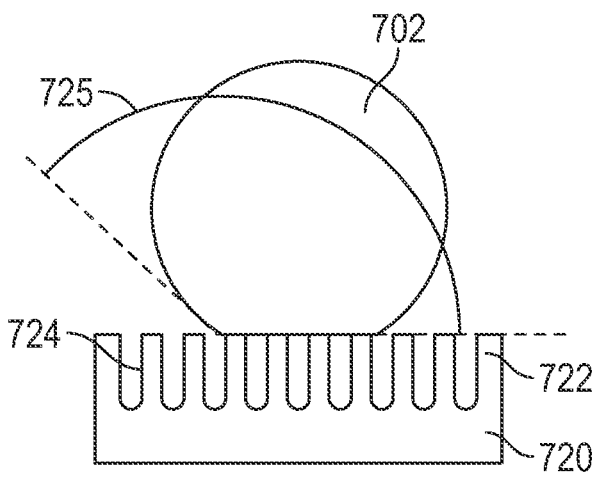

FIG. 7C shows a Cassie-Baxter state of interaction, similar to the state shown in FIGS. 3-5 above. A substrate 720 and a liquid medium 702 in a droplet form are shown. The substrate 720 includes a plurality of asperities 722 that are regularly spaced and define a number of spaces 724 between asperities 722. The substrate 710, asperities 722, and spaces 724 can be characterized by the equation above.

In FIG. 7C, the asperities 722 define a contact line density $\Lambda$ that is greater than the critical contact line density $\Lambda c$. As such, in FIG. 7C, none or very little of the liquid medium 702 penetrates into the spaces 724 between asperities 722 in the regular periodic physical structure. FIG. 7C shows a hydrophobic Cassie-Baxter state where a contact angle 725 is greater than 90 degrees. In one example, a hydrophobic state is defined by a contact angle 725 between 90 and 150 degrees. In one example, a more preferred hydrophobic state is defined by a contact angle 725 between 100 and 140 degrees.

In one example, a range of 100 to 140 provides a desired degree of low adhesion, as indicated by a higher contact angle, while also providing a robust coating that is not easily worn off a surface. Some materials with a lower contact angle are more robust than materials with a higher contact angle, therefore a tradeoff in material wear versus low adhesion is balanced with a range between 100 and 140 degrees.

In one example, the superhydrophobic state is defined by a contact angle 725 greater than 150 degrees. In higher contact angle states, a fluid in contact with the regular periodic physical structure rides up on top of the asperities 722 with a low surface area of actual interfacial contact, which facilitates fast dispersal of any fluid or contaminant that may come into contact with the surface. In a surgical context, material such as blood, tissue, etc. will be more easily flushed from a surface due riding on top of the regular periodic physical structure. In a more preferred example, the superhydrophobic state is defined by a contact angle 725 greater than 160 degrees. The higher contact angle provides lower resistance to lateral movement across the surface of material such as blood or tissue that is desired to be cleared from a local region.

Figure 7D:
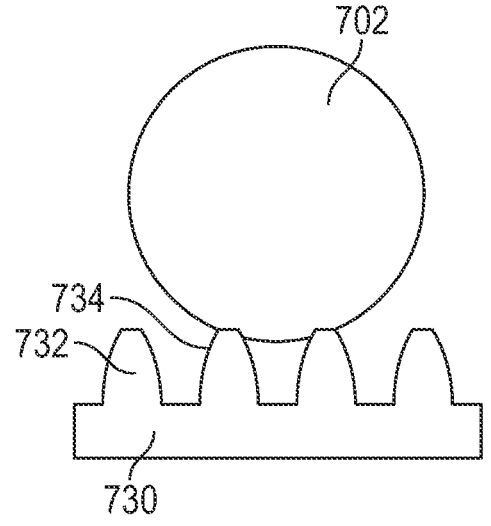

FIG. 7D shows a Lotus state of interaction. A substrate 730 and a liquid medium 702 in a droplet form are shown. The substrate 730 includes a plurality of asperities 732 that are regularly spaced and define a number of spaces 734 between asperities 732. The substrate 734, asperities 732, and spaces 734 can be characterized by the equation above. In the Lotus state, the liquid medium 702 is prevented from entering the spaces 734 between the asperities 732, resulting in low contact angle hysteresis (CAH) of less than 5 degrees at the moment a droplet runs off a substrate as defined below.

Figure 8A:
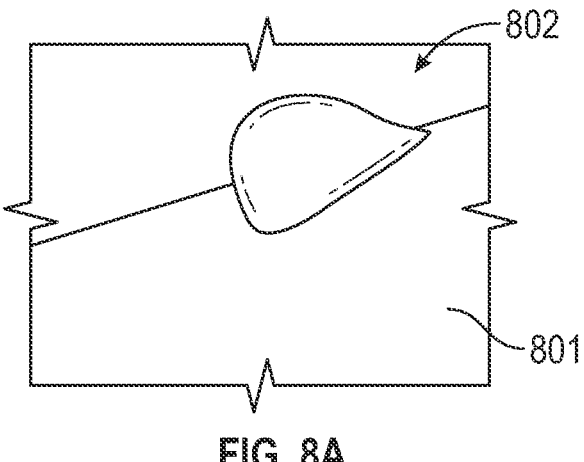
FIGS. 8A-8B illustrate methods of quantifying a surface with regular periodic physical structure in an example.
Figure 8B:
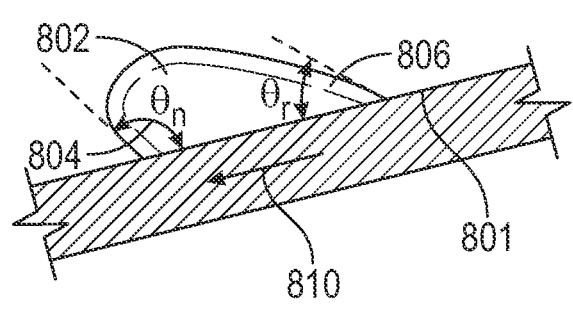

FIGS. 8A and 8B show a second method of quantifying a surface with regular periodic physical structure in addition to the equation above. In FIG. 8A, a droplet 802 is shown on a substrate 801. Examples of substrates 801 include coatings or processed bulk surfaces such that a surface of the substrate 801 forming an interface with the droplet 802 includes regular periodic physical structure as described in examples above. In a testing procedure, the substrate is tilted to an angle, and at some amount of tilting, the droplet ceases to adhere in its location, and runs off the substrate 801.

FIG. 8B shows an advancing contact angle 804 and a receding contact angle 806 of the droplet 802 as the substrate 801 is tilted. When the droplet runs off the substrate, it moves in direction 810. In a testing procedure, a difference can be measured between the advancing contact angle 804 and the receding contact angle 806. This difference is defined as the contact angle hysteresis (CAH).

In one example, if the CAH at the moment the droplet 802 runs off the substrate 801 is less than 5 degrees, then the material is nonadhesive. In one example, if the CAH at the moment the droplet 802 runs off the substrate 801 is greater than 5 degrees, then the material is adhesive.

VARIOUS NOTES & EXAMPLES

Example 1 is a device for smoke reduction in electrosurgery, the device comprising: a DC smoke ionization electrode, configured to be coupled to a DC voltage source to provide an ionizing DC voltage to a surgical site to ionize smoke particles at the surgical site; and a low adhesion layer at least partially covering the DC smoke ionization electrode, the low adhesion layer having a lower surface energy than an underlying portion of the DC smoke ionization electrode.

In Example 2, the subject matter of Example 1 optionally includes wherein the low adhesion layer has a surface energy less than that of an underlying portion of the DC smoke ionization electrode.

In Example 3, the subject matter of Example 2 optionally includes wherein the DC smoke ionization electrode is positionable within a patient, and a second electrode is positionable outside the patient, such that when an ionizing DC voltage is applied to the DC smoke ionization electrode and the second electrode, smoke particles located at the DC smoke ionization electrode are ionized.

In Example 4, the subject matter of any one or more of Examples 1-3 optionally include wherein the DC smoke ionization electrode is configured to receive a DC voltage from a power source.

In Example 5, the subject matter of any one or more of Examples 1-4 optionally include wherein the DC smoke ionization electrode is configured to disperse and ionize nearby smoke particles when exposed to a voltage above a first voltage threshold.

In Example 6, the subject matter of any one or more of Examples 1-5 optionally include wherein the low adhesion layer is configured to inhibit wetting of the DC smoke ionization electrode.

In Example 7, the subject matter of any one or more of Examples 1-6 optionally include Ohms.

In Example 8, the subject matter of any one or more of Examples 1-7 optionally include wherein the low adhesion layer comprises an electrical conductivity of less than that of an underlying portion of the DC smoke ionization electrode.

In Example 9, the subject matter of any one or more of Examples 1-8 optionally include.

In Example 10, the subject matter of any one or more of Examples 1-9 optionally include wherein the low adhesion layer comprises a superhydrophobic layer having a plurality of nidus points.

In Example 11, the subject matter of any one or more of Examples 1-10 optionally include wherein the low adhesion layer comprises one or more hydrophobic pillars located on the DC smoke ionization electrode.

In Example 12, the subject matter of any one or more of Examples 1-11 optionally include wherein the low adhesion layer comprises one or more polysiloxanes, fluorosilanes, or combinations thereof.

In Example 13, the subject matter of any one or more of Examples 1-12 optionally include nm, inclusive.

In Example 14, the subject matter of any one or more of Examples 1-13 optionally include nm, inclusive.

Example 15 is a system comprising: a device for smoke reduction in electrosurgery, the device including a smoke ionization electrode connectable to a patient, the smoke ionization electrode configured to ionize smoke particles in and around a surgical site, and a low adhesion layer at least partially covering the at smoke ionization electrode; and an DC power source electrically coupled to the device, configured to provide a DC voltage to the DC smoke ionization electrode.

In Example 16, the subject matter of Example 15 optionally includes wherein the low adhesion layer has a surface energy less than that of an underlying portion of the smoke ionization electrode.

In Example 17, the subject matter of any one or more of Examples 15-16 optionally include a second electrode of a polarity opposite the smoke ionization electrode.

Example 18 is a method of reducing smoke at a surgical site, the method comprising: applying a DC voltage to an DC smoke ionization electrode at the surgical site; and ionizing one or more smoke particles at the surgical site, wherein the DC smoke ionization electrode is at least partially covered by a low adhesion layer having a surface energy less than that of an underlying portion of the smoke ionization electrode.

In Example 19, the subject matter of Example 18 optionally includes reducing smoke at the surgical site while electrosurgery is ongoing at the surgical site.

In Example 20, the subject matter of any one or more of Examples 18-19 optionally include precipitating smoke particles onto surgical tissue as the smoke particles are ionized.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A device for smoke reduction in electrosurgery, the device comprising:

a DC smoke ionization electrode, configured to be coupled to a DC voltage source to provide an ionizing DC voltage to a surgical site to ionize smoke particles and to reduce a level of smoke present at the surgical site; and a radiofrequency (RF) electrical current conductive low adhesion layer comprising one or more hydrophobic pillars, on a substrate, at least partially covering the DC smoke ionization electrode; and wherein the DC smoke ionization electrode is further configured to be coupled to an RF energy source to receive RF energy and to also pass the RF electrical current through the RF electrical current conductive low adhesion layer to affect target tissue at the surgical site.

2. The device of claim 1, wherein the RF electrical current conductive low adhesion layer has a surface energy less than that of an underlying portion of the DC smoke ionization electrode.

3. The device of claim 2, wherein the DC smoke ionization electrode is positionable within a patient, and a second electrode is positionable outside the patient, such that when an ionizing DC voltage is applied to the DC smoke ionization electrode and the second electrode, smoke particles located at the DC smoke ionization electrode are ionized.

4. The device of claim 1, wherein the DC smoke ionization electrode is configured to receive a DC voltage from a power source.

5. The device of claim 1, wherein the DC smoke ionization electrode is configured to disperse and ionize nearby smoke particles when exposed to a voltage above a first voltage threshold.

6. The device of claim 1, wherein the RF electrical current conductive low adhesion layer is configured to inhibit wetting of the DC smoke ionization electrode.

7. The device of claim 1, wherein the RF electrical current conductive low adhesion layer comprises an impedance of less than about 10 Ohms.

8. The device of claim 1, wherein the RF electrical current conductive low adhesion layer comprises an electrical conductivity of less than that of an underlying portion of the DC smoke ionization electrode.

9. The device of claim 1, wherein the RF electrical current conductive low adhesion layer comprises a coefficient of friction of about 0.05 to about 0.15.

10. The device of claim 1, wherein the RF electrical current conductive low adhesion layer comprises a super-hydrophobic layer having a plurality of nidus points.

11. The device of claim 1, wherein the RF electrical current conductive low adhesion layer comprises one or more polysiloxanes, fluorosilanes, or combinations thereof.

12. The device of claim 1, wherein the RF electrical current conductive low adhesion layer has a thickness of between 1 nm and 300 nm, inclusive.

13. The device of claim 1, wherein the RF electrical current conductive low adhesion layer has a thickness of between 5 nm and 250 nm, inclusive.

14. A method of reducing smoke at a surgical site, the method comprising:

applying a DC voltage to a DC smoke ionization electrode at the surgical site; and providing an ionizing DC voltage to the surgical site to ionize smoke particles and to reduce smoke at the surgical site, wherein the DC smoke ionization electrode is at least partially covered by a radiofrequency (RF) electrical current conductive low adhesion layer comprising one or more hydrophobic pillars on a substrate, the RF electrical current conductive low adhesion layer having a surface energy less than that of an underlying portion of the smoke ionization electrode, and wherein the DC smoke ionization electrode is further configured to be coupled to an RF voltage source to receive RF energy and to also pass the RF electrical current through the RF electrical current conductive low adhesion layer to affect target tissue at the surgical site.

15. The method of claim 14, further comprising precipitating smoke particles onto surgical tissue as the smoke particles are ionized.

\* \* \* \* \*